US00PP19755P3

(12) United States Plant Patent
Drewlow

(10) Patent No.: US PP19,755 P3
(45) Date of Patent: Feb. 24, 2009

(54) ***KALANCHOE* PLANT NAMED 'FOREVER MIDI RED'**

(50) Latin Name: *Kalanchoe blossfeldiana*
Varietal Denomination: Forever Midi Red

(75) Inventor: Lyndon W. Drewlow, Lompoc, CA (US)

(73) Assignee: The Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/726,731

(22) Filed: Mar. 22, 2007

(65) Prior Publication Data

US 2008/0235837 P1 Sep. 25, 2008

(51) Int. Cl.
*A01H 5/00* (2006.01)

(52) U.S. Cl. ..... Plt./341
(58) Field of Classification Search ..... Plt./341
See application file for complete search history.

*Primary Examiner*—Annette H Para
(74) *Attorney, Agent, or Firm*—The Webb Law Firm

(57) ABSTRACT

'Forever Midi Red' is a new variety of *kalanchoe* that exhibits rich red flowers with a long blooming period.

1 Drawing Sheet

Botanical classification: *Kalanchoe blossfeldiana.*
Varietal denomination: 'Forever Midi Red'.

BACKGROUND OF THE INVENTION

The present invention comprises a new and distinct cultivar of *Kalanchoe blossfeldiana* known by the varietal name 'Forever Midi Red'. The new variety was discovered in Lompoc, Calif. The new variety is a result of cross breeding Seedling #98-231-2 (female parent) (unpatented) and Seedling #97-279-2 (male parent) (unpatented). The purpose of the breeding program was to develop a compact, long-lasting and self- branching cultivar. Comparisons between the new variety and its parents cannot be made, as the parental varieties no longer exist. The new variety was first asexually reproduced by tip cuttings in Lompoc, Calif. The new variety has been trial and field tested and has been found to retain its distinctive characteristics and remain true to type through successive propagations. Characteristics that distinguish the new variety from others known to the breeder include:

- Mounded and compact growing habit;
- Exhibits rich red flowers that do not fade;
- Early to flower, 9 to 9 ½ weeks from the start under short days;
- Able to be finished in 10 cm pots without growth regulators;
- Small leaf size allows for easier sleeving and shipping;
- Does not heat delay in night temperatures above 22° C.;
- Long blooming with indeterminant inflorescence;
- Highly self-branched without pinching; and
- Resistant to checking of the red flowers.

The new variety was grown in a 10 cm. container in Lompoc, California in a greenhouse under Dynaglass with 30% shade and 3500 to 4000 foot candles. The new variety was grown under natural, short days having temperatures of 20–22° C. and night temperatures of 16–18° C. The new variety initiates roots in 14 days at 21° C. The time to produce a rooted plant is 21 days at 21° C. Its rooting habit is dense and freely branching with fine and fibrous roots.

Further, the following Tables illustrate differences between the new variety and *Kalanchoe* varieties 'Aroi' (unpatented) and 'Molly'(U.S. Plant Pat. No. PP12,307), respectively:

TABLE 1

| Characteristics | 'Forever Midi Red' | 'Aroi' |
|---|---|---|
| Flower color | 45B | 42A |
| Stigma color | White with reddish tint | White |
| Leaf petiole length | 12 mm | 8 mm |
| Flower bud color | 44C near tip<br>144A near calyx end | 39A near tip<br>146B near calyx |
| Petal size | 8 mm long by 6 mm wide | 6 mm long by 5 mm wide |

TABLE 2

| Characteristics | 'Forever Midi Red' | 'Molly' |
|---|---|---|
| Flower color | 45B | Between 45B and 57B |
| Growth habit | Mounded | Upright |
| Stigma color | White with reddish tint | White |
| Plant height | 14 cm | 18 cm |
| Petal size | 8 mm long by 6 mm wide | 6 mm long by 5 mm wide |

DESCRIPTION OF THE DRAWING

The accompanying photographic drawing illustrates the new variety, with the color being as nearly true as is possible with color illustrations of this type.

DESCRIPTION OF THE PLANT

Figure 1:
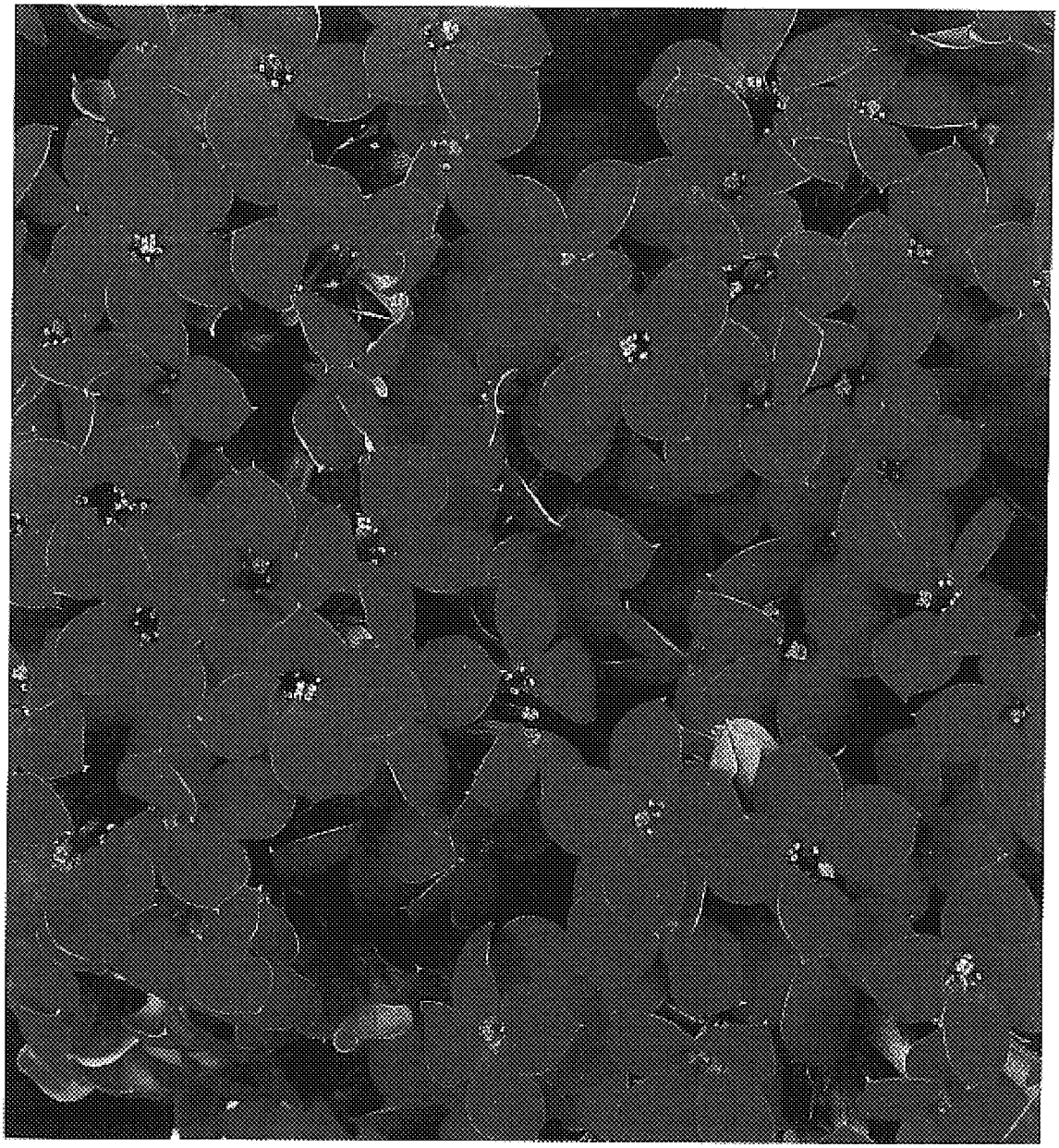

The following detailed description sets forth the characteristics of the new cultivar. The data which defines these characteristics were collected by asexual reproductions carried out in Lompoc, Calif. The color readings were taken indoors under 3500–4000 foot candles of light. The new variety was twelve weeks from the start of short days when described. Color references are primarily to the 1966 R.H.S. Colour Chart of The Royal Horticultural Society of London.

PLANT

Form: Mounded.
Height (from soil to top of flowers): 14 cm.
Plant diameter: 20–22 cm.
Vigor: Vigorous.
Branching habit: Highly self-branching.
Main stem:
*Color.*—146B.
*Texture.*—3 Glabrous.
*Length.*—10 cm.
*Diameter.*—1 cm.
*Internode length.*—12 mm.
*Strength.*—Strong.
Lateral branches:
*Color.*—146B.
*Texture.*—Glabrous.
*Length.*—Basal: 8 to 9 cm. Upper: 7–8 cm.
*Diameter.*—3 mm.
*Internode length.*—8–10 mm.
*Strength.*—Strong.
*Quantity.*—8–10.
Foliage:
*Arrangement.*—Opposite.
*Number of leaves per stem.*—2.
*Size of leaf.*—Length: 8 –9 cm. Width: 5–5.5 cm.
*Shape of leaf* (*generally*).—Ovate.
*Shape of apex.*—Acute to ovate.
*Shape of base.*—Acute to truncate.
*Texture.*—Glabrous, coriaceous and succulent.
*Apect.*—45° angle to stem.
*Margin type.*—Crenate, moderately lobed, shallow cut.
*Fragrance.*—None.
*Color.*—Young leaves: Upper surface: 146A. Lower surface: 146B. Mature leaves: Upper surface: 147A. Lower surface: 147B.
*Petiole.*—Length: 12 mm. Diameter: 6 mm. Color: 147A. Texture: Glabrous.
*Veins*: Venation pattern: Pinnate. Color: Upper surface: 147A. Lower surface: 147B.

FLOWER

Natural flowering season: January in Lompoc, Calif.—Short days start around October 15$^{th}$.
Flower type and habit: Single, alternate, cyme inflorescense.
Number of flowers per plant: 250 or more.
Time of day of flower opening: Morning, but it takes 3–5 days to fully open. Fragrance: None. Longevity: Up to 2 weeks, depending on environment. Flower height: 12 mm, including corolla tube. Flower diameter: 15 mm. Bud (described just before opening):
*Shape.*—Oblong.
*Diameter.*—3 mm.
*Length.*—12 mm.
*Color.*—44C near tip, 144A near calyx.
*Corolla.*—
*Diameter.*—4 mm.
*Depth.*—16 mm.
*Tube.*—Length: 10 mm. Diameter: 4 mm.
Petals:
*Arrangement.*—Whorl of 4 fused at base.
*Quantity.*—4.
*Length.*—8 mm.
*Width.*—6 mm.
*Shape.*—Ovate to round.
*Apex.*—Cuspidate.
*Margin.*—Entire.
*Texture.*—Smooth, soft.
*Color.*—Upper surface: 45B. Lower surface: 43C.
Sepals:
*Quantity.*—4.
*Shape.*—Lanceolate.
*Length.*—8 mm.
*Width*—2 mm.
*Color.*—146C.
Main stem peduncles.
*Length.*—18 mm.
*Diameter.*—3 mm.
*Color.*—146B.
*Texture.*—Glabrous.
*Orientation.*—5angle.
*Strength.*—Strong.
Pedicels:
*Length.*—3 mm.
*Width.*—3 mm.
*Color.*—146B.
Disease resistance: Present.
Seed production: None observed.
Fruit production: None observed.

REPRODUCTIVE ORGANS

Stamens:
*Number* (*per flower*).—8.
*Filament length.*—6 mm and approximately 3 mm fused to corolla tube.
*Anthers.*—Shape: Flat, elliptical. Length: Less than 1 mm. Color: Yellow-Green.
*Pollen.*—Color: Yellow. Amount: Abundant.
Pistils:
*Length.*—10 mm.
*Styles.*—Length: 3 mm. Color: Light yellow.
*Stigma.*—Shape: Flat. Color: White with a reddish tint when mature. Ovary color: 146C.

I claim:

1. A new and distinct variety of *kalanchoe* plant named 'Forever Midi Red' as is herein described and illustrated.

* * * * *

UNITED STATES PATENT AND TRADEMARK OFFICE

CERTIFICATE OF CORRECTION

PATENT NO. : PP 19,755 P3
APPLICATION NO. : 11/726731
DATED : February 24, 2009
INVENTOR(S) : Drewlow It is certified that error appears in the above-identified patent and that said Letters Patent is hereby corrected as shown below:

Column 4, under "Main stem peduncles. *Orientation*.—5angle." should read
-- *Orientation*.—45° angle --

Signed and Sealed this

Second Day of June, 2009

JOHN DOLL
*Acting Director of the United States Patent and Trademark Office*